United States Patent [19]

Sheldon et al.

[11] Patent Number: 4,522,967

[45] Date of Patent: Jun. 11, 1985

[54] HEAT SEALABLE WATER DISPERSIBLE ADHESIVE

[75] Inventors: Donald A. Sheldon, Outagamie County, Wis.; Bruce G. Stokes, Cherokee County, Ga.; Robert E. Weber, Cobb County, Ga.; Edwin G. Greenman, Cherokee County, Ga.

[73] Assignee: Kimberly-Clark Corporation, Neenah, Wis.

[21] Appl. No.: 618,810

[22] Filed: Jun. 8, 1984

[51] Int. Cl.$^3$ .......................... C08K 5/06; C08K 5/05; C08L 79/04

[52] U.S. Cl. .................................... 524/377; 525/185; 525/186; 525/222; 604/387

[58] Field of Search ....................... 524/377; 604/387; 525/186, 222, 185

[56] References Cited

U.S. PATENT DOCUMENTS

| | | | |
|---|---|---|---|
| 3,054,764 | 9/1962 | Walles et al. | 524/377 |
| 3,345,320 | 10/1967 | Uffner et al. | 524/377 |
| 3,442,845 | 5/1969 | Columbus et al. | 524/377 |
| 3,665,923 | 5/1972 | Champaigne | 604/387 |

*Primary Examiner*—Allan M. Lieberman

[57] ABSTRACT

A water dispersible heat activatable adhesive includes a polyethyloxazoline, a compatible water dispersible adhesive and an anti-blocking agent to prevent premature adhesion. This adhesive is particularly beneficial as a coating for flushable tampon tubes.

3 Claims, 1 Drawing Figure

HEAT SEALABLE WATER DISPERSIBLE ADHESIVE

FIELD OF THE INVENTION

This invention relates to a heat activatable water dispersible adhesive and particularly to the adhesive as a binder for flushable cellulosic products.

BACKGROUND OF THE INVENTION

During the past couple of decades, there has been increasing emphasis placed upon ease of disposability of consumer goods after the goods have performed their intended purpose. Examples of these consumer goods are facial or toilet tissue or containers which are made out of layered or corrugated paper. Other products such as sanitary napkins containing cellulosic material have been designed to be flushable but concessions have been made regarding adhesives. U.S. Pat. No. 3,665,923 discloses a flushable sanitary napkin in which the cover is dispersible and the absorbent component dissolvable. As is stated therein, however, the portion of the cover having garment attachment adhesive is neither dissolvable or dispersible. Clearly then, the segments of the cover which have adhesive applied to them will not easily disperse in a toilet.

Attempts have been made in the past to utilize water dispersible adhesives which are heat settable or heat activatable. These adhesives must provide a balance of solubility or dispersibility with adhesivity or cohesiveness. Since heat activatable adhesives tend to be organic, thermoplastic, polymeric and non-ionic, a careful balancing of properties and components is necessary. U.S. Pat. No. 3,891,584 describes a water dispersible hot melt adhesive containing 75-95 parts of a graft copolymer comprising a vinyl monomer and a polyalkylene oxide polymer in combination with a tackifying resin. While this adhesive composition does, apparently, disperse, it is exceedingly low in adhesivity for certain substrates such as nylon. This characteristic would inhibit its use for certain purposes such as for a flushable sanitary napkin garment attachment adhesive.

SUMMARY OF THE INVENTION

According to this invention, a water dispersible heat activatable adhesive is provided which is particularly designed for use with paper tampon tubes and similar otherwise flushable articles. The heat activatable adhesive of this invention comprises sufficient polyethyloxazoline to form a tacky surface on a flushable substrate, a compatible water dispersible plasticizer and a protective anti-blocking component. When used in conjunction with a convolutely wound paper tampon tube, the anti-blocking component serves to inhibit the tacky properties otherwise inherent in the plasticized polyethyloxazoline. This allows the winding of such a tampon tube or other coated paper roll goods without the premature unwanted adherence of one layer to another.

DETAILED DESCRIPTION OF THE INVENTION AND DRAWINGS

Figure 1:
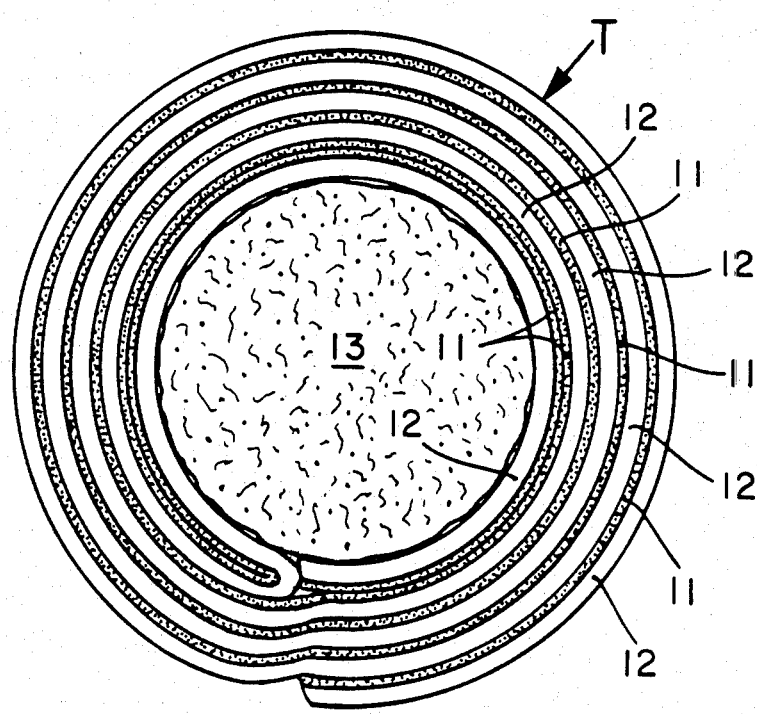

One use for this invention may be more readily understood by reference to the drawings in which FIG. 1 is a top plan view of a multiple convolutely wound tampon tube T with a tampon present.

Tampon 13 is positioned within tube T which is formed by several layers or windings of a paper 12, e.g., kraft paper, coated with the heat activatable adhesive 11 of this invention. The paper 12 used to produce water flushability is generally standard bleached paper with very little wet strength or other additives so that it rapidly absorbs water and redisperses. The base kraft paper may have a coating on the side opposite the adhesive coating 11 to produce either a high surface gloss or, alternatively, matte appearance. This coating should have a low binder to pigment ratio for rapid water absorption with the binder being a water dispersible or redispersible material such as starch. Such binders and finishes are well known in the art.

Polyethyloxazoline has been found useful in molecular weights ranging from 50,000 to 500,000 with a molecular weight of approximately 300,000 being preferred. (The limits of molecular weight of polyethyloxazoline are determined by availability of the compound in the market place. Molecular weights of this material lower than 50,000 and above 500,000 are not readily obtainable.) Polyethyloxazoline is available from Dow Chemical Company, Midland, Mich. and sold under the trade designation DOW XA-10874.

Plasticizers usable in accordance with this invention must be compatible with polyethyloxazoline, must have a low glass transition temperature (Tg). It is generally preferred that the glass transition temperature be below about 10° C. Currently preferred plasticizers are ethylene-vinylacetate copolymers: examples are Airflex 141 and 142 sold by Air Products, Allentown, Pa. Ethylene-vinylacetate copolymers containing between 10-30% ethylene may be used, with the higher the percentage of ethylene monomer present in the copolymer being reflective of lower Tg values. Suitable ratios of polyethyloxazoline to ethylene-vinylacetate are from about 25 to 87.5 parts polyethyloxazoline to about 75 to 12.5 parts of ethylene-vinylacetate by weight. At the higher levels of polyethyloxazoline, the adhesive coating tends to become hard and brittle while as the ethylene-vinylacetate percentage increases, the adhesive tends to lose its water sensitivity. A presently preferred ratio is 50 parts polyethyloxazoline to 50 parts ethylene-vinylacetate.

Other suitable plasticizers were vinylacetate acrylic copolymers such as Nacrylic 4441 sold by National Starch Corporation, Bridgewater, N.J. and acrylic polymers such as Hycar 26120 sold by B. F. Goodrich of Cleveland, Ohio. Vinylacetate acrylic copolymers have been tested at a ratio of 25 to 75 parts of polyethyloxazoline to 75 parts to 25 parts vinylacetate acrylic copolymers. The same ratio has been used for acrylic polymers but in the case of the acrylic polymer they are neutralized prior to use with sodium hydroxide or other permanent base to maintain their water dispersibility. Generally the pH is adjusted to about 9. Currently preferred ratios in each instance are 50 parts of plasticizer to 50 parts polyethyloxazoline.

As mentioned previously, anti-blocking agents are used to prevent premature adhesion of layered rolled products at ambient temperatures. Suitable anti-blocking agents are polyethylene glycol and polypropylene glycol of moderate molecular weights. Polyethylene glycols ranging in molecular weights from 2,000 to 17,500 have been used as anti-blocking agents, successfully. The polyethylene glycols have been added to the adhesive formula in a ratio of 5-35 parts anti-blocking agents to 100 total parts of polyethyloxazoline plasticizer mixture.

Polyethylene glycols having a molecular weight below 600 tend not to provide sufficient anti-blocking properties. The currently preferred anti-blocking formulation is one containing 15 parts of polyethylene glycol with a molecular weight of 3350 and 3 parts of polyethylene glycol having a molecular weight of 600 per 100 parts of the polyethyloxazoline plasticizer mixture. Polyethyloxazoline is generally adhesively activated in the currently formulations at a temperature of about 400° F. Sufficient adhesion for purposes of maintaining the convolutely wound tampon tube configuration was achieved in all ranges of plasticizer, polyethyloxazoline and anti-blocking agents. This was also true from the standpoint of water dispersibility with the trends and properties as the extremes of each of the ranges were reached as described above.

We claim:

1. A water dispersible heat activatable adhesive comprising:
   25-87.5 parts by weight polyethyloxazoline
   75-12.5 parts by weight polyethyloxazoline compatible water dispersible plasticizer with a Tg below about 10° C. and an anti-blocking agent at a level of 5 to 35 parts per 100 parts of the polyethyloxazoline plasticizer mixture said anti-blocking agent selected from the class consisting of moderate molecular weight polyethylene glycol and moderate molecular weight polypropylene glycol.

2. The adhesive according to claim 1 wherein the plasticizer is an ethylene-vinylacetate copolymer with 10-30% by weight of ethylene.

3. The adhesive according to claims 1 wherein the plasticizer is present at a level of 25-75 parts by weight and selected from the group consisting of water dispersible acrylic polymers and water dispersible vinylacetate acrylic copolymers.

* * * * *